United States Patent [19]

Evans et al.

[11] Patent Number: 4,496,565
[45] Date of Patent: Jan. 29, 1985

[54] CHROMANS AND CHROMENES, COMPOSITIONS AND HYPERTENSIVE METHOD

[75] Inventors: John M. Evans, Roydon; Valerie A. Ashwood, Harlow, both of England

[73] Assignee: Beecham Group p.l.c., England

[21] Appl. No.: 542,658

[22] Filed: Oct. 17, 1983

[30] Foreign Application Priority Data

Oct. 19, 1982 [GB] United Kingdom ................ 8229789
May 18, 1983 [GB] United Kingdom ................ 8313677

[51] Int. Cl.³ .................. A61K 31/425; A61K 31/54; C07D 413/04; C07D 417/04
[52] U.S. Cl. .................. 514/222; 514/228; 514/229; 514/232; 514/233; 514/234; 514/236; 514/230; 514/254; 514/369; 514/376; 514/392; 514.237; 544/6; 544/58.2; 544/70; 544/151; 544/230; 544/316; 544/318; 544/372; 544/373; 544/376; 548/147; 548/186; 548/187; 548/216; 548/299; 548/231; 548/318
[58] Field of Search ................ 544/58.2, 70, 151, 230, 544/316, 318, 372, 373, 376, 6; 548/147, 186, 187, 216, 229, 231, 318; 424/248.5, 248.52, 248.54, 248.55, 248.56, 248.57, 250, 251, 270, 272, 273 R, 248.58, 246

[56] References Cited

U.S. PATENT DOCUMENTS 4,363,811 12/1982 Evans et al. ................ 548/525
4,366,163 12/1982 Evans et al. ................ 424/267
4,446,113 5/1984 Evans et al. ................ 424/267

FOREIGN PATENT DOCUMENTS 46652 3/1982 European Pat. Off. .

OTHER PUBLICATIONS

Lap et al., Aust. J. Chem., 1979, 32, pp. 619-636.

Primary Examiner—Robert W. Ramsuer
Attorney, Agent, or Firm—Jacobs & Jacobs

[57] ABSTRACT

Compounds of formula (I):

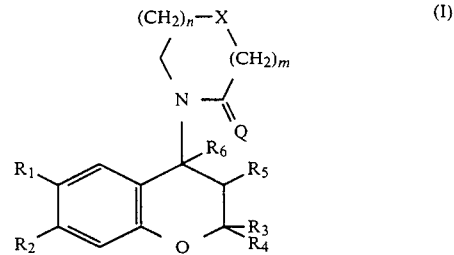

a pharmaceutically acceptable salt or solvate thereof having anti-hypertensive activity, a process for their preparation and their use as pharmaceuticals.

9 Claims, No Drawings

CHROMANS AND CHROMENES, COMPOSITIONS AND HYPERTENSIVE METHOD

The present invention relates to novel chromans and chromenes having pharmacological activity, to a process for preparing them, to pharmaceutical compositions containing them, and to their use in the treatment of mammals.

U.S. Pat. Nos. 4,110,347 and 4,119,643 and 4,251,537 and European Patent Publications 28 064 and 28 449 disclose classes of chromans that are described as having blood pressure lowering activity or anti-hypertensive activity.

A further class of chromans, and their corresponding chromenes, has now been discovered which are characterised by the presence of a hetero atom-containing lactam or thiolactam ring, the nitrogen atom of which substitutes the chroman or chromene in the 4-position. In addition, such chromans and chromenes have been found to have blood pressure lowering activity.

Accordingly, the present invention provides a compound of formula (I):

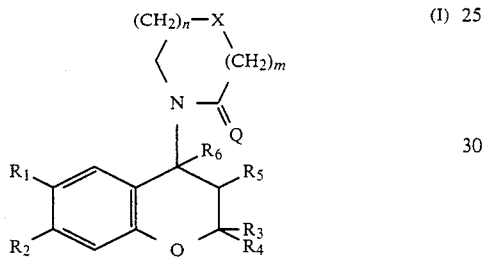

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkyl-hydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-8}$ acyloxy and $R_6$ is hydrogen or $R_5$ and $R_6$ together are a bond;
Q is O or S;
m is an integer from 0 to 2 and n is an integer from 0 to 2 such that m+n is 1 or 2;
X is O or S, or N-$R_7$, $R_7$ being hydrogen, $C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen; mono- or bi-cyclicheteroarylcarbonyl; the lactam or thiolactam group being trans to the $R_5$ group when $R_5$ and $R_6$ are not a bond; or, when one or the other of $R_1$ and $R_2$ is an amino or an amino-containing group, or when X is NR$_7$ and $R_7$ is hydrogen, a pharmaceutically acceptable salt or solvate thereof.

There is a group of compounds within formula (I) wherein $R_1$, $R_2$, $R_3$, $R_4$, $R_6$, m and n are as defined in formula (I); $R_5$ is hydroxy, $C_{1-6}$ alkoxy, $C_{1-8}$ acyloxy or together with $R_6$ forms a bond and X is O or S or, when m is 1 or 2, N-$R_7$, $R_7$ being hydrogen, $C_{1-6}$ alkyl, phenylcarbonyl or benzylcarbonyl optionally substituted in the phenyl ring by $C_{1-6}$ alkyl, $C_{1-6}$ alkoxy or halogen; or a pharmaceutically acceptable salt thereof.

There is a further group of compounds within formula (I) wherein:
one of $R_1$ and $R_2$ is hydrogen and the other is selected from the class of $C_{2-7}$ alkanoyl, $C_{2-7}$ alkoxycarbonyl, $C_{2-7}$ alkylcarbonyloxy, $C_{1-6}$ alkyl-hydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{2-7}$ alkanoylamino, $C_{2-7}$ alkoxycarbonylamino or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$-alkoxysulphonylamino or ethylenyl terminally substituted by $C_{2-7}$ alkanoyl, nitro or cyano, or —C(alkyl)NOH or —C(alkyl)NNH$_2$;
$R_5$ is hydroxy, alkyloxy having from 1 to 3 carbon atoms or acyl having from 1 to 8 carbon atoms;
$R_6$ is hydrogen;
X is O or S or (when m=1 or 2), NR$_7$ wherein $R_7$ is $C_{1-6}$ alkyl; and the remaining variables are as defined in formula (I).

When one of $R_1$ and $R_2$ is hydrogen, the other is preferably selected from the class of $C_{1-6}$ alkylcarbonyl, $C_{1-6}$ alkoxycarbonyl, $C_{1-6}$ alkylcarbonyloxy, $C_{1-6}$ alkyl-hydroxymethyl, nitro or cyano. In particular, when one of $R_1$ and $R_2$ is hydrogen, the other is preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-8}$ acyloxy and $R_6$ is hydrogen, a preferred class of $R_5$ is unsubstituted carboxylic acyloxy, such as unsubstituted aliphatic acyloxy or benzoyloxy. However, it is preferred that $R_5$ and $R_6$ together are a bond, or, in particular, that $R_5$ is hydroxy and $R_6$ is hydrogen.

Q is preferably oxygen.

m is often 0 or 1.

n is often 0 or 1.

When X is $NR_7$, suitable values of $R_7$ include hydrogen, methyl, ethyl, n- and iso-propyl, n-, sec- and tert-butyl, benzyl, phenylcarbonyl or benzylcarbonyl optionally substituted in the phenyl ring by methyl, methoxy, chloro or bromo; furylcarbonyl, thienylcarbonyl, pyrrolylcarbonyl or indolylcarbonyl. Preferably $R_7$ is hydrogen, methyl, n-butyl, acetyl, benzyl, benzylcarbonyl, phenylcarbonyl or furylcarbonyl. Most preferably $R_7$ is methyl.

Within formula (I) is a sub-group of preferred compounds of formula (II):

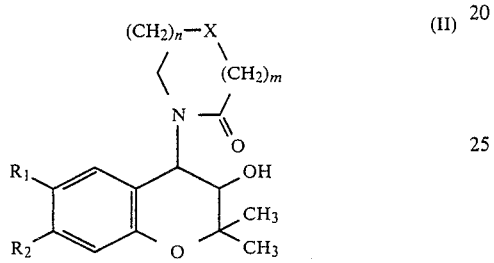

(II)

wherein m, X and Q are as hereinbefore defined, one of $R_1{}^1$ and $R_2{}^1$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro or cyano and n is 1 or 2; the lactam group or thiolactam group being trans to the hydroxy group, or, when X is $NR_7$ and $R_7$ is hydrogen, a pharmaceutically acceptable salt thereof.

Compounds of formula (II), wherein one of $R_1$ and $R_2$ is hydrogen and the other is nitro or cyano, are greatly preferred. Additionally, compounds of formula (II), wherein $R_2$ is hydrogen and $R_1$ is one of the substituents as defined hereinbefore, are preferred. Consequently the most preferred compounds are those of formula (II), wherein $R_1$ is nitro or cyano and $R_2$ is hydrogen.

There is a sub-group of compounds within formula (II) wherein X is O or S and the remaining variables are as defined. There is a further sub-group of compounds within formula (II) wherein X is $NR_7$ as defined. Suitable and preferred $R_7$ are as described under formula (I). When X is $NR_7$, preferably m and n are both 1.

The compounds of formula (I) and (II) cover both a 2-oxo-3-oxazolidin-1-yl substituent (when n=1, m=0), a 2-oxamorpholin-1-yl or 2-oxopiperazinyl substituent (when n=1, m=1) and a tetrahydro-2-pyrimidone substituent (when n=2, m=0).

Examples of a pharmaceutically acceptable salt of a compound of formulae (I) and (II), when one or the other of $R_1$ and $R_2$ is an amino or an amino-containing group or, when X is $NR_7$ and $R_7$ is hydrogen, include the hydrochloride and hydrobromide salts.

Preferably, a compound of formula (I) or (II) is in substantially pure form.

The compounds of formula (I) and (I), wherein $R_5$ is hydroxy, $C_{1-6}$ alkoxy or $C_{1-8}$ acyloxy and $R_6$ is hydrogen, are disymmetric and, therefore, can exist as stereoisomers. The present invention extends to all such stereoisomers individually and as mixtures, such as racemic modifications.

Examples of compounds of formula (I) include the compounds prepared in the Examples hereinafter. Of these, those that are particularly preferred include 6-cyano-2,2-dimethyl-3,4-dihydro-trans-4(2-oxo-3-oxazolidin-1-yl)-2H-benzo[b]pyran-3-ol, 6-cyano-2,2-dimethyl-3,4-dihydro-trans-4-(2-oxomorpholin-1-yl)-2H-benzo[b]pyran-3-ol, 6-cyano-3,4-dihydro-2,2-dimethyl-trans-4-(N-4-methylpiperazin-1-one)-2H-benzo[b]-pyran-3-ol, trans-4-(N-acetylpiperazin-2-one)-6-cyano-3,4-dihydro-2,2-dimethyl-2H-benzo[b]pyran-3-ol, 6-cyano-3,4-dihydro-2,2-dimethyl-trans-4-(1-piperazin-2-one)-2H-benzo[b]pyran-3-ol, trans-4-(N-benzyl-2-oxopiperazinyl)-6-cyano-3,4-dihydro-2,2-dimethyl-2H-benzo[b]pyran-3-ol, trans-4-(N-butylpiperazin-2-one)-6-cyano-3,4-dihydo-2,2-dimethyl-2H-benzo[b]pyran-3-ol, and trans-4-(N-benzoyl-2-oxopiperazinyl)-6-cyano-3,4-dihydro-2,2-dimethyl-2H-benzo[b]pyran.

The compounds of formulae (I) and (II) have asymmetric centres and therefore exist in optically active isomeric forms. The present invention extends to all such forms and to mixtures of them.

The invention also provides a process for the preparation of a compound of formula (I) which process comprises the reaction of a compound of formula (III):

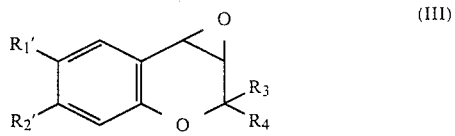

(III)

wherein $R_1'$ and $R_2'$ are $R_1$ and $R_2$, as defined hereinbefore, or a group or atom convertible thereto, and $R_3$ and $R_4$ are as defined hereinbefore, with an anion of formula (IV):

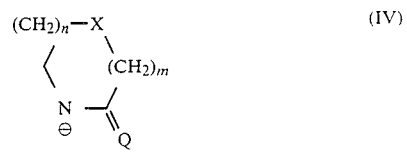

(IV)

wherein m, n and X are as hereinbefore defined; in the case where $R_1'$ or $R_2'$ is a group or atom convertible into $R_1$ or $R_2$, converting the group or atom into $R_1$ or $R_2$; optionally converting $R_1$ or $R_2$ in the resulting compound of formula (I) into another $R_1$, or optionally alkylating or acylating, the resulting compound of formula (I), wherein $R_5$ is hydroxy, to give another compound of formula (I), wherein $R_5$ is $C_{1-6}$ alkoxy or $C_{1-8}$ acyloxy, optionally dehydrating the resulting compound of formula (I), wherein $R_5$ and $R_6$ are hydroxy and hydrogen respectively to give another compound of formula (I), wherein $R_5$ and $R_6$ together are a bond; reducing a compound of formula (I) wherein $R_5$ and $R_6$ together are a bond to give a compound wherein $R_5$ and $R_6$ are both hydrogen, optionally thiating the carbonyl group in the lactam ring of the resulting compound of formula (I) to give another compound of formula (I), wherein Q is sulphur; in the case where X is $NR_7$, optionally converting $R_7$ into another $R_7$; and, when one or the other of $R_1$ and $R_2$ in the resulting compound of formula (I) is amino or an amino-containing group, or when X is $NR_7$ and $R_7$ is hydrogen, optionally forming a pharmaceutically acceptable salt.

In order to generate the anion of formula (IV), the reaction is, preferably, carried out in the presence of a base, such as sodium hydride. It may also be carried out in an inert solvent, such as dimethylsulphoxide, at a low, medium or high temperature.

The reaction leads specifically to the compound of formula (I), wherein the lactam group is trans to the $R_5$ group.

Conversions of an aromatic group into $R_1$ or $R_2$, as defined hereinbefore, are generally known in the art of aromatic chemistry. For example, if the optional thiation reaction is to be carried out in order to obtain a compound of formula (I), wherein one or the other of $R_1$ and $R_2$ is a carbonyl-containing group and Q is sulphur, it is preferred to use the corresponding compound of formula (II), wherein $R_1'$ or $R_2'$ is a protected carbonyl-containing group, and, after reaction and thiation, to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Examples of an optional conversion of $R_1$ or $R_2$ in the resulting compound of formula (I) into another $R_1$ or $R_2$, as hereinbefore defined, include the optional conversion of an α-hydroxyethyl group into acetyl by oxidation, the optional conversion of a chloro atom into an amino group by amination, the optional conversion of an amino group into an amino group substituted by one or two $C_{1-6}$ alkyl or by $C_{2-7}$ alkanoyl, or the optional conversion of a hydrogen atom into a nitro group by nitration.

The optional alkylation or acylation of the resulting compound of formula (I), wherein $R_5$ is hydroxy, to give another compound of formula (I), wherein $R_5$ is $C_{1-6}$ alkoxy or $C_{1-8}$ acyloxy, may be carried out in accordance with conventional alkylating or acylating reagents. For example, alkylation may be carried out using an alkyl iodide in an inert solvent, such as toluene, in the presence of a base, such as potassium hydroxide, and alkylation may be carried out using a carboxylic acid chloride or anhydride in a non-hydroxylic solvent in the presence of condensation promoting agent, such as dicyclohexylcarbodiimide.

The optional dehydration of a resulting compound of formula (I), wherein $R_5$ and $R_6$ are hydroxy and hydrogen respectively, into another compound of formula (I), wherein $R_5$ and $R_6$ together are a bond, may be carried out in accordance with conventional dehydration conditions, for example, by using a dehydrating agent, such as sodium hydride, in an inert solvent, such as dry tetrahydrofuran, at reflux temperature.

The reduction of an $R_5/R_6$ bond may be carried out by conventional catalytic hydrogenation using Palladium on charcoal.

The optional thiation of the carbonyl group in the lactam ring of the resulting compound of formula (I) to give another compound of formula (I), wherein X is sulphur, is, preferably, carried out with conventional thiation agents, such as hydrogen sulphide, phosphorus pentasulphide and Lawesson's reagent (p-methoxyphenylthiophosphine sulphide dimer). The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

In the case where X is $NR_7$, examples of the optional conversion of $R_7$ into another $R_7$ include the optional conversion of $R_7$, when hydrogen, into $R_7$, when $C_{1-6}$ alkyl, by direct alkylation or by acylation and reduction or by reductive alkylation, and the optional conversion of $R_7$, when hydrogen, into $R_7$, when phenylcarbonyl or other arylcarbonyl or benzylcarbonyl optionally substituted as defined hereinbefore, by benzoylation or by arylacetylation. With such conversions, it would be desirable to protect any amino or amino-containing group for $R_1$ or $R_2$ and then to deprotect them after acylation. It is preferred that $R_7$ in formula (IV) is $R_7$ in formula (I), except that when $R_7$ in formula (I) is hydrogen, in which case $R_7$ in formula (IV) a protecting group, preferably acetyl, which may be removed by conventional hydrolysis.

The optional formation of a pharmaceutically acceptable salt, when one or the other of $R_1$ and $R_2$ in the resulting compound of formula (I) is amino or an amino-containing group, or when X is $NR_7$ and $R_7$ is hydrogen, may be carried out conventionally.

A compound of formula (III) may be prepared, preferably in situ, by reacting a compound of formula (V):

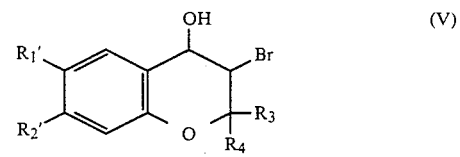

wherein $R_1'$, $R_2'$, $R_3$ and $R_4$ are as hereinbefore defined and the hydroxy group is trans to the bromo atom, with a base, such as potassium hydroxide, in a solvent, such as ether or aqueous dioxan.

Compounds of formula (V) are known and may be prepared in accordance with any appropriate known process, for example, by the process described in the aforementioned U.S. patents and European patent publications. Schematically, such process can be depicted thus.

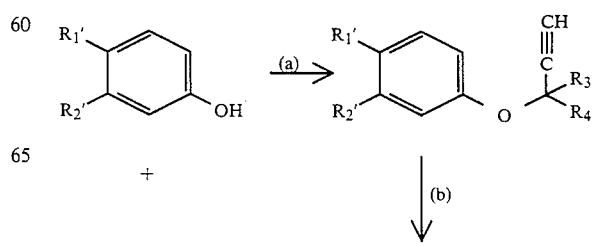

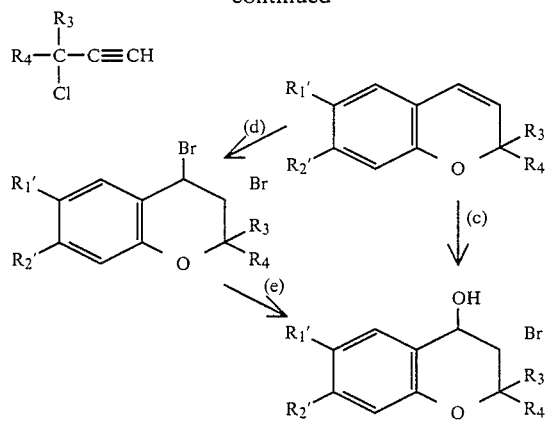

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process can produce mixtures of compounds during reaction (b) owing to the two sites available for ring formation. It is therefore advisable to remove any of the undesired compound by, for example, chromatography, before reaction (c) or (d).

Instead of carrying out the subsequent conversion of a group or atom into hydrogen or group or atom into one of the class of substituents defined for the other of $R_1$ and $R_2$ it is greatly preferred that any such conversions are carried out at an earlier stage, preferably on the chromene produced after reaction (b) above. In other words, it is preferred that, for the processes of the invention $R_1'$ and $R_2'$ are $R_1$ and $R_2$ respectively.

As mentioned previously, the compounds of formula (I) exist in optically active forms, and the processes of the present invention produce mixtures of such forms. The individual isomers may be separated one from another by chromatography using a chiral phase. Alternatively, an asymmetric synthesis would offer a route to the individual form.

The compounds of formula (I), and especially those of formula (II), have been found to have blood-pressure lowering activity. They are therefore potentially useful as a pharmaceutical in the treatment of hypertension.

The present invention accordingly provides a pharmaceutical composition which comprises a compound of the formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of the formula (I) and a pharmaceutically acceptable carrier.

The compositions are preferably adapted for oral administration. however, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials.

Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of formula (I) and especially of formula (II) for use in the treatment of hypertension.

The present invention yet further provides a method of treating hypertension in mammals including man, which comprises administering to the suffering mammal an anti-hypertensive effective amount of a compound of formula (I) or a pharmaceutically acceptable salt thereof or a pharmaceutical composition of the invention.

The following examples relate to the preparation of compounds of formula (I).

EXAMPLE 1

6-Cyano-2,2-dimethyl-3,4-dihydro-trans-4-(2-oxo-3-oxazolidin-1-yl)-2H-benzo[b]pyran-3-ol (E1)

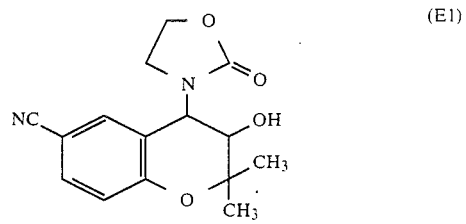

To a mixture of 6-cyano-3,4-dihydro-2,2-dimethyl-3,4-epoxy-2H-benzo[b]pyran (1.0 g, the preparation of which was described in U.K. Pat. No. 1,511,187) and 2-oxazolidone (0.43 g) stirred in dimethyl sulphoxide (30 ml, previously dried over 4 Å molecular sieve) was added sodium hydride (0.15 g, 80% dispersion in oil). Stirring at room temperature was continued for 6 hours before addition of water (50 ml) and extraction with ethyl acetate. Drying and evaporation and recrystallisation of the crude solid obtained gave 6-cyano-2,2-dimethyl-3,4-dihydro-3,4-dihydro-trans-4-(2-oxo-3-oxazolidin-1-yl)-2H-benzo[b]pyran-3-ol as colourless crystals of m.p. 232°–234° C.

NMR (DMSOd$_6$)δ: 1.19 (3H,s), 1.45 (3H,s), 3.18 (1H,q,J=8,8,8 Hz), 3.54 (1H,q,J=8,8,8 Hz) overlapping 3.71 (1H,q,J=11,5 Hz) collapsing to a doublet of J=11 Hz on D$_2$O addition, 4.38 (2H,m,two J of 8 Hz visible), 4.67 (1H,d,J=11 Hz), 5.88 (1H,d,J=5 Hz) exchangeable with D$_2$O, 6.95 (1H,d,J=9 Hz), 7.56 (1H, narrow m) overlapping, 7.65 (1H,m, one J of 2 Hz visible).

EXAMPLE 2

6-Cyano-2,2-dimethyl-3,4-dihydro-trans-4-(2-oxomorpholin-1-yl)-2H-benzo[b]pyran-3-ol (F2)

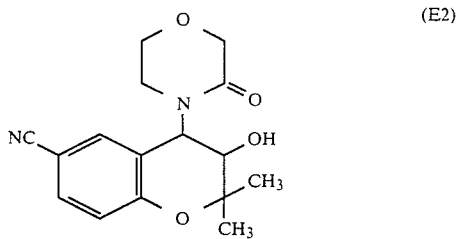

To a mixture of 6-cyano-3,4-dihydro-2,2-dimethyl-3,4-epoxy-2H-benzo[b]pyran (0.5 g) and 2-oxomorpholine (0.25 g) stirred in dimethyl sulphoxide (20 ml, previously dried over 4 Å molecular sieves) at room temperature, was added sodium hydride (0.08 g, 80% dispersion in oil). After stirring for 16 hours, water (40 ml) was added and the aqueous phase was extracted with ethyl acetate. Water washing, drying over anhydrous magnesium sulphate, filtration and evaporation gave a white solid (0.21 g). Two recrystallisations gave the title compound as colourless crystals of m.p. 249°–250° C.

NMR (CDCl$_2$)δ: 1.30 (3H,s), 1.55 (3H,s), 2.80–4.15 (7H, complex series of m), 5.83 (1H, d, J=12 Hz), 6.92 (1H, d, J=9 Hz), 7.33 (1H, narrow m), 7.48 (1H, q, J=9,2 Hz).

EXAMPLE 3

6-Cyano-2,2-dimethyl-3,4-dihydro-trans-4-(2-oxo-3-thiazolidin-1-yl)-2H-benzo[b]-pyran-3-ol (E3)

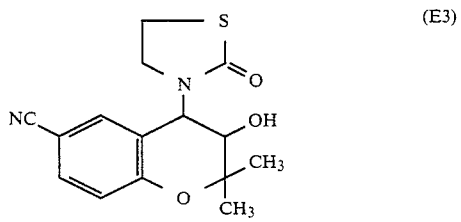

To a mixture of 6-cyano-3,4-dihydro-2,2-dimethyl-3,4-epoxy-2H-benzo[b]pyran (0.59 g) and 2-oxothiazolidine (0.38 g) stirred in dry dimethyl sulphoxide (30 ml) was added sodium hydride (0.11 g, 80% dispersion in oil). After stirring at room temperature for 6 hours, water (50 ml) was added and the aqueous phase extracted with ethyl acetate. The organic layer was washed with water and brine and dried over magnesium sulphate. Filtration and evaporation gave a gum (0.35 g) which was chromatographed (chromatotron, pentane-ethyl acetate gradient elution, 2 mm silica gel) to give a fraction (105 mg) which was recrystallised from ethyl acetate-pentane to give the title compound (32 mg) as crystals of m.p. 239°–240° C. Mass spectrum M+ at m/z 286.0781 Calcd. for C$_{15}$H$_{14}$N$_2$O$_2$S 286.0776.

EXAMPLE 4

6-Cyano-2,2-dimethyl-3,4-dihydro-trans-4-(2-oxothiomorpholin-1-yl)-2H-benzo[b]-pyran-3-ol (E4)

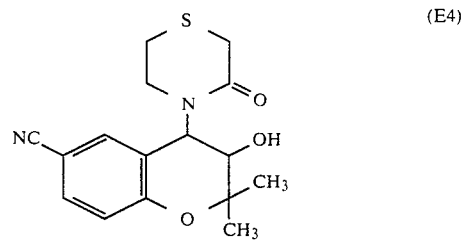

In a similar manner to that described in example (3), the epoxide was treated with 2-ketothiomorpholine to give a crude product, which on recrystallisation from ethyl acetate gave the title compound (260 mg) as crystals of m.p. 238°–240° C.

Mass spectrum M+ at m/z 318.1035 Calcd. for C$_{16}$H$_{18}$N$_2$O$_3$S 318.1038.

EXAMPLE 5

6-Cyano-3,4-dihydro-2,2-dimethyl-trans-4-(N-4-methylpiperazin-1-one)-2H-benzo[b]pyran-3-ol (E5)

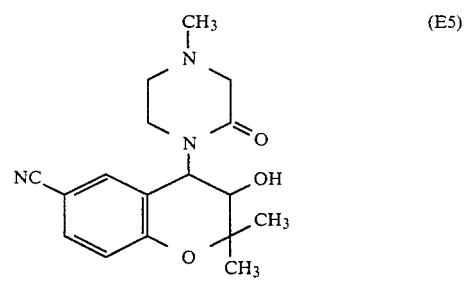

To a mixture of 6-cyano-3,4-dihydro-2,2-dimethyl-3,4-epoxy-2H-benzo[b]pyran (0.58 g) and 4-N-methylpiperazin-2-one (0.33 g) in dry dimethylsulphoxide (15 ml) was added sodium hydride (0.09 g, 80% dispersion in oil). After stirring at room temperature for 4 hours, water was added and the aqueous phase extracted with ethyl acetate. The organic layer was washed with water and brine and dried over magnesium sulphate. Filtration and evaporation and combination with the product of a second run starting with epoxide (0.5 g), gave a gum (0.61 g) which was purified on the chromatotron to give a fraction (0.35 g) which on recrystallisation from ethyl acetate gave the title compound (125 mg) of m.p. 196°–197.5° C.

NMR (CDCl$_3$+D$_2$O)δ: 1.29 (3H,s), 1.54 (3H,s), 2.39 (3H,s), 2.40–3.50 (6H, Series of m), 3.79 (1H,d,J=10 Hz)), 5.85 (1H,d,J=10 Hz), 6.88 (1H,d,J=9 Hz), 7.29 (1H,d,J=2 Hz), 7.44 (1H,q,J=9,2 Hz).

EXAMPLE 6

Trans-4-(N-acetylpiperazin-2-one)-6-cyano-3,4-dihydro-2,2-dimethyl-2H-benzo[b]pyran-3-ol (E6)

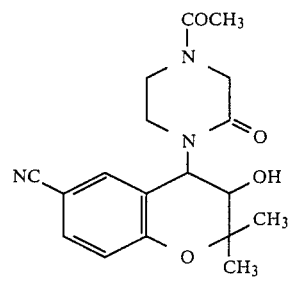

(E6)

In a similar manner to that described in example 5, the epoxide of the earlier examples was treated with 4-N-acetylpiperazin-2-one. After 2 hours reaction the usual work up and recrystallisation from ethyl acetate gave the title compound of m.p. 230°–231° C., as the hemihydrate.

Mass spectrum M+ m/z 343.1436.

Calcd for $C_{18}H_{21}N_3O_4$: 343.1426.

EXAMPLE 7

6-Cyano-3,4-dihydro-2,2-dimethyl-trans-4-(1-piperazin-2-one)-2H-benzo[b]pyran-3-ol (E7)

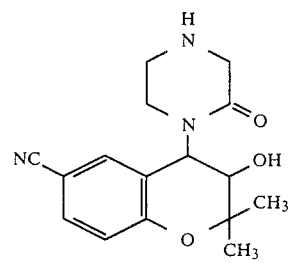

(E7)

The compound of example (6) (150 mg) was heated under reflux in ethanol (9 ml) contaning 5N HCl (5 ml) for 2 hours. Basification of the cooled solution with 10% NaOH solution and dilution with water (50 ml), and extraction with ethyl acetate gave, after drying over anhydrous magnesium sulphate, filtration, and evaporation, a crude product (120 mg) which was recrystallised from ethyl acetate-pentane to give the title compound of m.p. 207°–210° C. as the hemihydrate.

Mass spectrum M+—$H_2O$ at m/z 283.1323 Calcd. for $C_{16}H_{17}N_3O_2$: 283.1321.

EXAMPLE 8

Trans-4-(N-benzyl-2-oxopiperazinyl)-6-cyano-3,4-dihydro-2,2-dimethyl-2H-benzo[b]pyran-3-ol (E8)

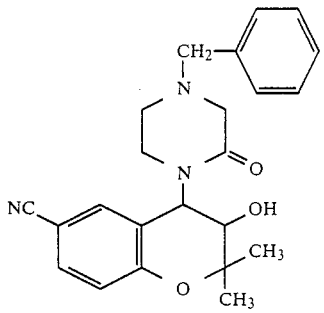

(E8)

The epoxide (425 mg) of the earlier examples was treated in a similar manner to that described in example (5) with 4-N-benzylpiperazin-2-one (400 mg) and sodium hydride (5.0 mg, 80% dispersion in oil) in dimethyl sulphoxide (20 ml). The usual reaction gave the title compound after chromatography and recrystallisation from ethyl acetate as crystals (140 mg) of m.p. 178°–179.5° C. Mass spectrum M+ at m/z 391.1893 Calcd. for $C_{23}H_{25}N_3O_8$: 391.1896.

EXAMPLE 9

Trans-4-(N-benzoyl-2-oxopiperazinyl)-6-cyano-3,4-dihydro-2,2-dimethyl-2H-benzo[b]pyran (E9)

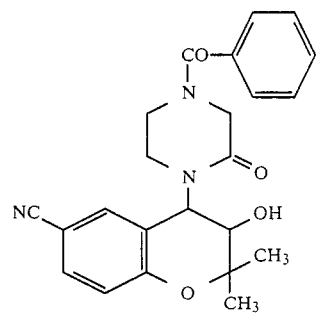

(E9)

As in example (8) the epoxide was treated with 4-N-benzoylpiperazin-2-one to furnish, after chromatography and recrystallisation from ethyl acetate, the title compound as crystals of m.p. 250°–251° C.

Mass spectrum M+ at m/z 405.1677.

Calcd. for $C_{23}H_{23}N_3O_4$: 405.1688.

EXAMPLE 10

6-Cyano-2,2-dimethyl-4-(2-ketothiazolidinyl)-2H-benzo[b]pyran (E10)

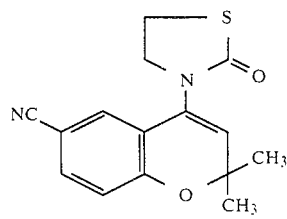

(E10)

Further investigation of other chromatographic fractions in the preparation of the compound of example (3) gave a solid having a higher Rf on TLC than the compound of example (3). Recrystallisation from ethyl acetate-pentane gave the title compound of m.p. 132.5°–133.5° C.

NMR (CDCl$_3$)δ: 1.51 (6H,s), 3.35–4.00 (4H, symmetrical m), 5.75 (1H,s), 6.90 (1H,d,J=9 Hz), 7.32 (1H,d,J=2 Hz), 7.47 (1H,q,J=9,2 Hz).

EXAMPLE 11

6-Cyano-3,4-dihydro-2,2-dimethyl-trans-4-(4-(2-furoyl)-2-oxopiperazinyl)-2H-benzo[b]-pyran-3-ol (E11)

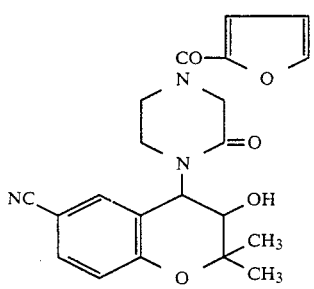

Following the procedure in example (5) the epoxide was reacted with 4-(2-furoyl)-piperazin-2-one to yield the title compound, after chromatography and recrystallisation from ethyl acetate/pentane, as crystals of m.p. 226°–229° C., as the hemihydrate.

Mass spectrum M+—H$_2$O at m/z 377.1371
Calcd. for C$_{21}$H$_{19}$N$_3$O$_4$: 377.1375.

EXAMPLE 12

6-Cyano-3,4-dihydro-2,2-dimethyl-trans-4-(N-3-methyltetrahydro-2-pyrimidone)-2H-benzo[b]-pyran-3-ol (E12)

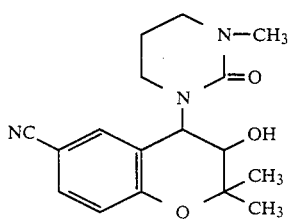

As in example (5) the epoxide (1.5 g) and 3-methyltetrahydro-2-pyrimidone (0.85 g) in dry dimethyl sulphoxide (20 mls) was treated with sodium hydride (0.24 g, 80% dispersion in oil) and stirred for 3 hrs. Water (50 mls) was added and the aqueous phase extracted with chloroform. The organic layer was washed with water and brine, dried over magnesium sulphate, filtered and evaporated to give a gum (1.5 g). Chromatography, and recrystallisation from ethyl acetate/pentane gave the title compound as crystals (0.16 g) of m.p. 187°–188.5° C.

NMR (CDCl$_3$+D$_2$O)δ: 1.31 (3H, s), 1.53 (3H, s), 1.75–2.20 (2H, m), 2.65–3.25 (2H, m) overlapping, 3.04 (3H, s), 3.36 (2H, t, J=6 Hz), 3.68 (1H, d, J=10 Hz), 5.71 (1H, d, J=11 Hz), 6.88 (1H, d, J=10 Hz), 7.35–7.55 (2H, m).

EXAMPLE 13

6-Cyano-2,2-dimethyl-4-(N-3-methyltetrahydro-2-pyrimidone)-2H-benzo[b]-pyran (E13)

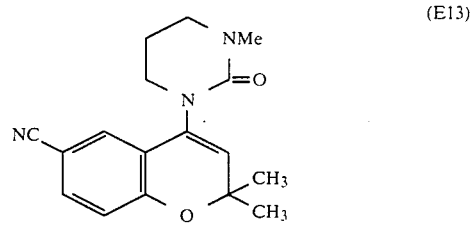

The preparation of the compound in example (12) also yielded a compound with higher Rf on TLC than the product of example (12). Recrystallisation from ethyl acetate/pentane gave the title compound as crystals (73 mgs) of
m.p. 185°–187° C.

NMR (CDCl$_3$)δ: 1.50 (6H, s), 1.90–2.35 (2H, m), 3.00 (3H, s), 3.25–3.60 (4H, m), 5.62 (1H, s), 6.84 (1H, d, J=9 Hz), 7.30 (1H, d, J=2 Hz), 7.41 (1H, q, J=9,2 Hz).

EXAMPLE 14

6-Acetyl-3,4-dihydro-2,2-dimethyl-trans-4-(N-4-fluorobenzoyl)-2-oxopiperazinyl)-2H-benzo[b]-pyran-3-ol (E14)

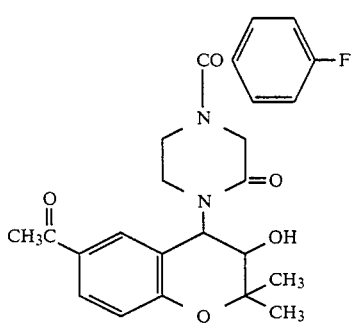

To a mixture of 6-acetyl-3,4-dihydro-2,2-dimethyl-3,4-epoxy-2H-benzo[b]pyran (0.5 g) and N-4-fluorobenzoylpiperazin-2-one (0.5 g) in dry dimethyl-sulphoxide (20 ml) was added sodium hydride (0.07 g, 80% dispersion in oil). After stirring for 4 hours, the usual work up followed by chromatography and recrystallisation from ethyl acetate gave the title compound (0.15 g) as crystals of m.p. 147.5°–150° C.

NMR (CDCl$_3$)δ: 1.27 (3H), 1.53 (3H), 2.54 (3H), 3.00–4.50 (6H series of m,) overlapping, 3.74 (1H, d, J=10 Hz), 5.88 (1H, d, J=10 Hz), 6.89 (1H, d, J=9 Hz), 7.13 (2H, t, J=9 Hz), 7.48 (2H, q, J=9, 6 Hz), 7.65 (1H, br s), 7.79 (1H, q, J=9, 2 Hz).

EXAMPLE 15

Trans-4-(n-butylpiperazin-1-one)-6-cyano-3,4-dihydro-2,2-dimethyl-2H-benzo[b]pyran-3-ol (E15)

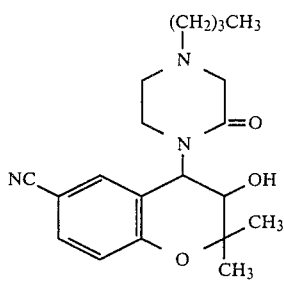

To a mixture of 6-cyano-3,4-dihydro-2,2-dimethyl-3,4-epoxy-2H-benzo[b]pyran (0.80 g) and 4-n-butylpiperazin-2-one (0.60 g) in dry dimethylsulphoxide (30 ml) was added sodium hydride (0.12 g, 80% dispersion in oil). The reaction mixture was stirred at room temperature for 4.5 hours, then diluted with water and extracted with ethyl acetate. The organic layer was washed with water and dried over anhydrous magnesium sulphate. Filtration and evaporation gave a mixture (0.95 g) which was purified on the chromatotron to give a pure fraction (0.25 g) which was recrystallised from ethyl acetatepentane to give the title compound (0.15 g) as the hydrate of m.p. 90°–93° C.

Mass spectrum M+ at m/z 357.2057. Calcd. for $C_{20}H_{27}N_3O_3$: 357.2052.

Pharmacological Data

Systolic blood pressures were recorded by a modification of the tail cuff method described by I. M. Claxton, M. G. Palfreyman, R. H. Poyser, R. L. Whiting, European Journal of Pharmacology, 37, (1976). W+W BP recorder, model 8005, was used to display pulses. Prior to all measurements rats were placed in a heated environment (33.5°+0.5° C.) before transfer to a restraining cage. Each determination of blood pressure was the mean of at least 6 readings. Spontaneously hypertensive rats (ages 12–18 weeks) with systolic blood pressures 170 mmHg were considered hypertensive.

| Compound of Example 1 | Time Post Dose Hours | % Change in Systolic Blood Pressure | % Change in Heart Rate |
|---|---|---|---|
| 6 rats | | | |
| Dose 3 mg/kg | 1 | −19 ± 6 | −3 ± 5 |
| po | 2 | −12* ± 8 | −2 ± 4 |
| Initial Blood Pressure | 4 | −29 ± 8 | −11 ± 3 |
| 222 + 6 mmHg | 6 | −21 ± 5 | −7 ± 4 |
| Initial Heart Rate | — | — | — |
| 488 + 20 beats/min | | | |

*1 rat had no measurable pulse

| Compound of Example 7 | Time Post Dose Hours | % Change in Systolic Blood Pressure | % Change in Heart Rate |
|---|---|---|---|
| 6 rats | | | |
| Dose 0.3 mg/kg | 1* | −53 ± 8 | −1 ± 3 |
| po | 2** | −35 ± 10 | −1 ± 4 |
| Initial Blood Pressure | 4** | −28 ± 11 | −6 ± 3 |
| 230 + 5 mmHg | 6** | −17 ± 13 | −9 ± 5 |
| Initial Heart Rate | | | |
| 474 + 10 beats min. | | | |

*1 rat had no measurable pulse
**2 rats had no measurable pulse.

Other compounds of the examples were also found to be active in this test.

Toxicity

No toxic effects were observed in the above test.

We claim:

1. A compound of formula (I):

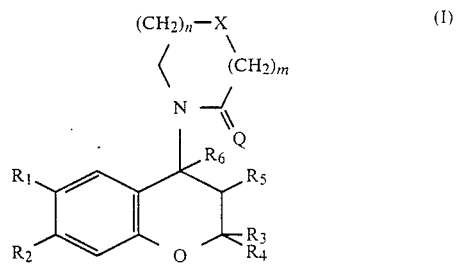

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C(C$_{1-6}$ alkyl)NOH or —C(C$_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-8}$ acyloxy and $R_6$ is hydrogen or $R_5$ and $R_6$ together are a bond;
Q is O or S;
m is an integer from 0 to 2 and n is an integer from 0 to 2 such that m+n is 1 or 2;
X is O or S, or N—R$_7$, R$_7$ being hydrogen, $C_{1-9}$ alkyl, $C_{2-7}$ alkanoyl, phenylC$_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen; mono- or bi-cycliheteroarylcarbonyl; the lactam or thiolactam group being trans to the $R_5$ group when $R_5$ and $R_6$ are not a bond; or, when one or the other of $R_1$ and $R_2$ is an amino or an amino-containing group, or when X is $NR_7$ and $R_7$ is hydrogen, a pharmaceutically acceptable salt or solvate thereof.

2. A compound according to claim 1 of formula (II):

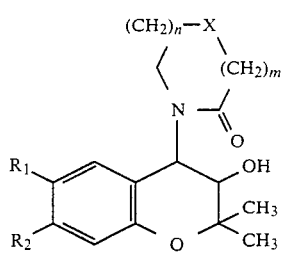

(II)

wherein m, X and Q are as defined in claim 1, one of $R_1{}^1$ and $R_2{}^1$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro or cyano and n is 1 or 2; the lactam group or thiolactam group being trans to the hydroxy group, or, when X is $NR_7$ and $R_7$ is hydrogen, a pharmaceutically acceptable salt thereof.

3. A compound according to claim 2 wherein X is O or S.

4. A compound according to claim 2 wherein X is $NR_7$.

5. A compound according to claim 4 wherein m and n are both 1.

6. A compound according to claim 1 wherein one of $R_1$ and $R_2$ is hydrogen and the other is nitro or cyano.

7. A compound selected from the group consisting of:
6-cyano-2,2-dimethyl-3,4-dihydro-trans-4-(2-oxo-3-oxazolidin-1-yl)-2H-benzo[b]pyran-3-ol;
6-cyano-2,2-dimethyl-3,4-dihydro-trans-4-(2-oxomorpholin-1-yl)-2H-benzo[b]pyran-3ol;
6-cyano-2,2-dimethyl-3,4-dihydro-trans-4-(2-oxo-3-thiazolidin-1-yl)-2H-benzo[b]-pyran-3-ol;
6-cyano-2,2-dimethyl-3,4-dihydro-trans-4-(2-oxothiomorpholin-1-yl)-2H-benzo[b]-pyran-3-ol;
6-cyano-3,4-dihydro-2,2-dimethyl-trans-4-(N-4-methylpiperazin-1-one)-2H-benzo[b]-pyran-3-ol;
trans-4-(N-acetylpiperazine-2-one)-6-cyano-3,4-dihydro-2,2-dimethyl-2H-benzo[b]pyran-3-ol;
6-cyano-3,4-dihydro-2,2-dimethyl-trans-4-(1-piperazine-2-one)-2H-benzo[b]pyran-3-ol;
trans-4-(N-benzyl-2-oxopiperazinyl)-6-cyano-3,4-dihydro-2,2-dimethyl-2H-benzo[b]pyran-3-ol;
trans-4-(N-benzoyl-2-oxopiperazinyl)-6-cyano-3,4-dihydro-2,2-dimethyl-2H-benzo[b]pyran;
6-cyano-2,2-dimethyl-4-(2-ketothiazolidinyl)-2H-benzo[b]pyran;
6-cyano-3,4-dihydro-2,2-dimethyl-trans-4-(4-furoyl)-2-oxopiperazinyl)-2H-benzo[b]-pyran-3-ol;
6-cyano-3,4-dihydro-2,2-dimethyl-trans-4-(N-3-methyltetrahydro-2-pyrimidone)-2H-benzo[b]-pyran-3-ol;
6-cyano-2,2-dimethyl-4-(N-3-methyltetrahydro-2-pyrimidone)-2H-benzo[b]-pyran;
6-acetyl-3,4-dihydro-2,2-dimethyl-trans-4-(N-4-fluorobenzoyl-2-oxopiperazinyl)-2H-benzo[b]-pyran-3-ol;
and
trans-4-(n-butylpiperazin-1-one)-6-cyano-3,4-dihydro-2,2-dimethyl-2H-benzo[b]pyran-3-ol.

8. A pharmaceutical composition comprising a pharmaceutically effective amount of compound according to claim 1 or a pharmaceutically acceptable salt thereof and a pharmaceutically acceptable carrier.

9. A method of treatment of hypertension in mammals including humans comprising the administration of a pharmaceutically effective amount of a compound according to claim 1 or a pharmaceutically acceptable salt thereof to the sufferer.

* * * * *